United States Patent [19]

Brown

[11] Patent Number: 5,167,220
[45] Date of Patent: Dec. 1, 1992

[54] SYSTEMS AND METHODS FOR MAINTAINING A CLEAR VISUAL FIELD DURING ENDOSCOPIC PROCEDURES

[76] Inventor: Cathy K. Brown, 821 E. 8475 South, Sandy, Utah 84094

[21] Appl. No.: 564,933

[22] Filed: Aug. 9, 1990

[51] Int. Cl.⁵ .......................... A61B 1/00; A61M 25/02
[52] U.S. Cl. ......................................... 128/4; 604/280
[58] Field of Search ........................... 128/3, 4, 5, 6, 7; 604/258, 264, 266, 280, 179

[56] References Cited

U.S. PATENT DOCUMENTS

| | | | |
|---|---|---|---|
| 2,557,377 | 6/1951 | Ganz | 32/28 |
| 2,776,487 | 1/1957 | Brown | 32/28 |
| 3,850,162 | 11/1974 | Iglesias | 128/6 |
| 3,856,000 | 12/1974 | Chikama | 128/6 |
| 3,903,877 | 9/1975 | Terada | 128/6 |
| 4,146,019 | 3/1979 | Bass et al. | 128/6 |
| 4,281,646 | 8/1981 | Kinoshita | 128/6 |
| 4,311,134 | 1/1982 | Mitsui et al. | 128/6 |
| 4,433,692 | 2/1984 | Baba | 128/660 |
| 4,576,145 | 3/1986 | Tsuno et al. | 128/6 |
| 4,615,333 | 10/1986 | Taguchi | 128/6 |
| 4,616,631 | 10/1986 | Takahashi | 128/6 |
| 4,841,952 | 6/1989 | Sato et al. | 128/6 |

OTHER PUBLICATIONS

Richard Wolf Medical Instruments Corp., *New and Old Generation in Sinuscopy* (published in U.S.A.), publication date unknown.
Richard Wolf Medical Instruments Corp. telescope bridges, suction/irrigation sheaths, and suction irrigation handle, publication date unknown.
Karl Storz, *Nasal Instruments,* pp. ORL 17 & 19, publication date unknown.

*Primary Examiner*—William H. Grieb
*Attorney, Agent, or Firm*—Berne S. Broadbent

[57] ABSTRACT

A nasal sinus endoscope system and method. The system comprises a nasal sinus endoscope having a distal viewing window. A resilient tube is attached to the endoscope such that the distal end of the tube is in proximity to the distal viewing window of the endoscope, and a syringe is connected to the proximal end of the resilient tube for selectively forcing fluid through the tube and out of the distal end thereof. The distal end of the resilient tube preferably forms an oblique angle with respect to a longitudinal axis of the tube, and the resilient tube is attached to the endoscope such that the oblique opening formed by the distal end of the tube substantially faces the endoscope. The resilient tube is attached to the endoscope by means of suitable fasteners, such as, for example, elastic bands which encircle both the tube and the endoscope.

38 Claims, 1 Drawing Sheet

SYSTEMS AND METHODS FOR MAINTAINING A CLEAR VISUAL FIELD DURING ENDOSCOPIC PROCEDURES

BACKGROUND

1. The Field of the Invention

This invention relates to endoscopes and endoscopic procedures. More specifically, this invention relates to systems and methods for maintaining a clear visual field during endoscopic procedures and, in particular, during nasal sinus endoscopic procedures.

2. The Background Art

In order to examine an interior bodily organ or region, an endoscope is commonly used. Generally speaking, an endoscope is a rigid or semi-rigid device comprising an optical system. One end of the endoscope is adapted to be inserted into the organ or region to be examined, and a light transmission system is also typically incorporated to illuminate the organ or region. The physician can thus perform the necessary bodily examination by looking through the endoscope.

Following an endoscopic examination, a physician may determine that surgery is required. The surgeon may then use an endoscope to view the surgical site, while at the same time performing the surgical procedure with appropriate surgical instruments. In this way, the surgeon is able to perform the required operation using forceps, scissors, knives, or other surgical instruments, while continuously observing the operation through the endoscope.

During endoscopic procedures of the type outlined above, it is common for the lens or viewing window of the scope to become periodically obstructed by blood or other body fluids or by tissue fragments or fog. Of course, it is then necessary to clear the visual field before the examination or surgery can continue.

A typical way to maintain a clear visual field during endoscopic procedures is to periodically remove the endoscope from the body and wash or wipe the endoscope's viewing lens. The endoscope can thereafter be reinserted into the body, and the examination or surgery can continue. Unfortunately, however, this relatively simple procedure suffers from a number of significant disadvantages.

For example, in using the above-outlined procedure, a surgeon must periodically interrupt the examination or surgery in order to clear the visual field. The endoscope must then be carefully repositioned in the patient's body before the examination or surgery can continue As a result, the examination or surgery is prolonged. In addition, due to the fact that the proper insertion and placement of an endoscope is usually somewhat delicate, the repeated removal and reinsertion of the endoscope poses a significantly increased risk of injuring the patient.

Further, maintaining a clear visual field in the manner described above is quite awkward. Surgical instruments may tend to get in the way. Moreover, the surgeon's attention becomes divided, and the surgeon is forced to focus a significant amount of attention on the instruments and equipment being used, rather than on the surgical procedures being performed.

In an effort to alleviate some of the foregoing concerns, those skilled in the art have developed endoscopes and endoscope accessories which include integral irrigation and/or suction channels. During nasal sinus endoscopic procedures, for example, it is common to employ a sheath surrounding the endoscope through which an irrigation fluid may be injected so as to clear the visual field. Although many surgeons seem to prefer such devices to the use of the conventional techniques described above, significant drawbacks remain.

The need to operate a separate mechanism associated with the endoscope in order to clear the visual field still typically requires the surgeon's attention, thus still requiring the periodic interruption of the examination or surgery. Additionally, many available suction/irrigation mechanisms are somewhat complicated, making them both difficult and/or time consuming to assemble and awkward and difficult to handle during use. This again results in an increase in the time required for the examination or surgery and in a need for the surgeon to devote significant surgical time and attention to instrumentation.

In addition, the use of integral irrigation/suction systems can increase the diameter of the endoscope, which, in some cases, can become a significant disadvantage. During nasal sinus endoscopic procedures, for example, surgical space is very limited. Surgical instruments are typically four to five millimeters in diameter, while a typical endoscope may be from about two and one-half to about four millimeters in diameter. The use of a separate irrigating sheath which will, of course, further increase the size of the endoscope may thus significantly restrict the scope's access to and/or movement within the surgical site and, as a result, limit the scope's viewing area and ultimate effectiveness.

Irrigation sheaths and similar accessories for endoscopes can also be relatively bulky and heavy. This often makes the scope hard to control and may, consequently, increase the potential risk that the scope may penetrate and cause injury to an adjacent organ or bodily region. The increased weight of the scope also accelerates hand fatigue during surgery, and, when using such devices, it is not uncommon for a surgeon's had to begin shaking with fatigue before the surgery is completed.

Further, the prior art irrigation/suction accessories for integral use with endoscopes are usually quite expensive. Being non-disposable, they must also be sterilized prior to each use. Also, careful maintenance is required, since the use of conventional saline irrigation solutions renders the metal parts highly susceptible to rust. This further increases the cost and inconvenience of such devices.

BRIEF SUMMARY AND OBJECTS OF THE INVENTION

In view of the foregoing, it is a primary object of the present invention to provide a system and method for maintaining a clear visual field adjacent the distal viewing window of an endoscope which is simple to assemble and easy to handle and use.

It is also a principal object of the present invention to provide a system and method for maintaining a clear visual field adjacent the distal viewing window of an endoscope which does not require the use of separate, bulky instruments, thereby leaving the surgeon's hands free to use surgical instruments, suction, and other devices without interruption.

Further, it is an object of the present invention to provide a system and method for maintaining a clear visual field adjacent the distal viewing window of an endoscope which has minimal weight and bulk.

It is an additional object of the present invention to provide a system and method for maintaining a clear visual field adjacent the distal viewing window of an endoscope which allows an irrigation tube to be placed along the endoscope in virtually any manner suited to the specific surgeon's needs.

It is a still further object of the present invention to provide a system and method for maintaining a clear visual field adjacent the distal viewing window of an endoscope which is inexpensive and disposable.

Consistent with the foregoing objects, and in accordance with the invention as embodied and broadly described herein, a system is disclosed for maintaining a clear visual field adjacent the distal viewing window of an endoscope. In accordance with one presently preferred embodiment of the present invention, the system comprises a resilient tube having a proximal end and a distal end, the tube being attached along the endoscope such that the distal end of the tube is in proximity to the distal viewing window of the endoscope. Means (such as, for example, a syringe), is connected to the proximal end of the resilient tube for selectively forcing fluid through the tube and out of the distal end thereof. The visual field adjacent the distal viewing window of the endoscope is thus washed and maintained clear.

Advantageously, the distal end of the resilient tube may form an oblique angle with respect to a longitudinal axis of the tube. In such case, the resilient tube is preferably attached to said endoscope such that the oblique opening formed by the distal end of the tube substantially faces the endoscope. Washing of the viewing window of the endoscope is thus facilitated since the fluid will tend to flow from the tube and along the endoscope

BRIEF DESCRIPTION OF THE DRAWINGS

The foregoing and other objects and features of the present invention will become more fully apparent from the following description and appended claims, taken in conjunction with the accompanying drawings Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENT

Figures 1, 2:
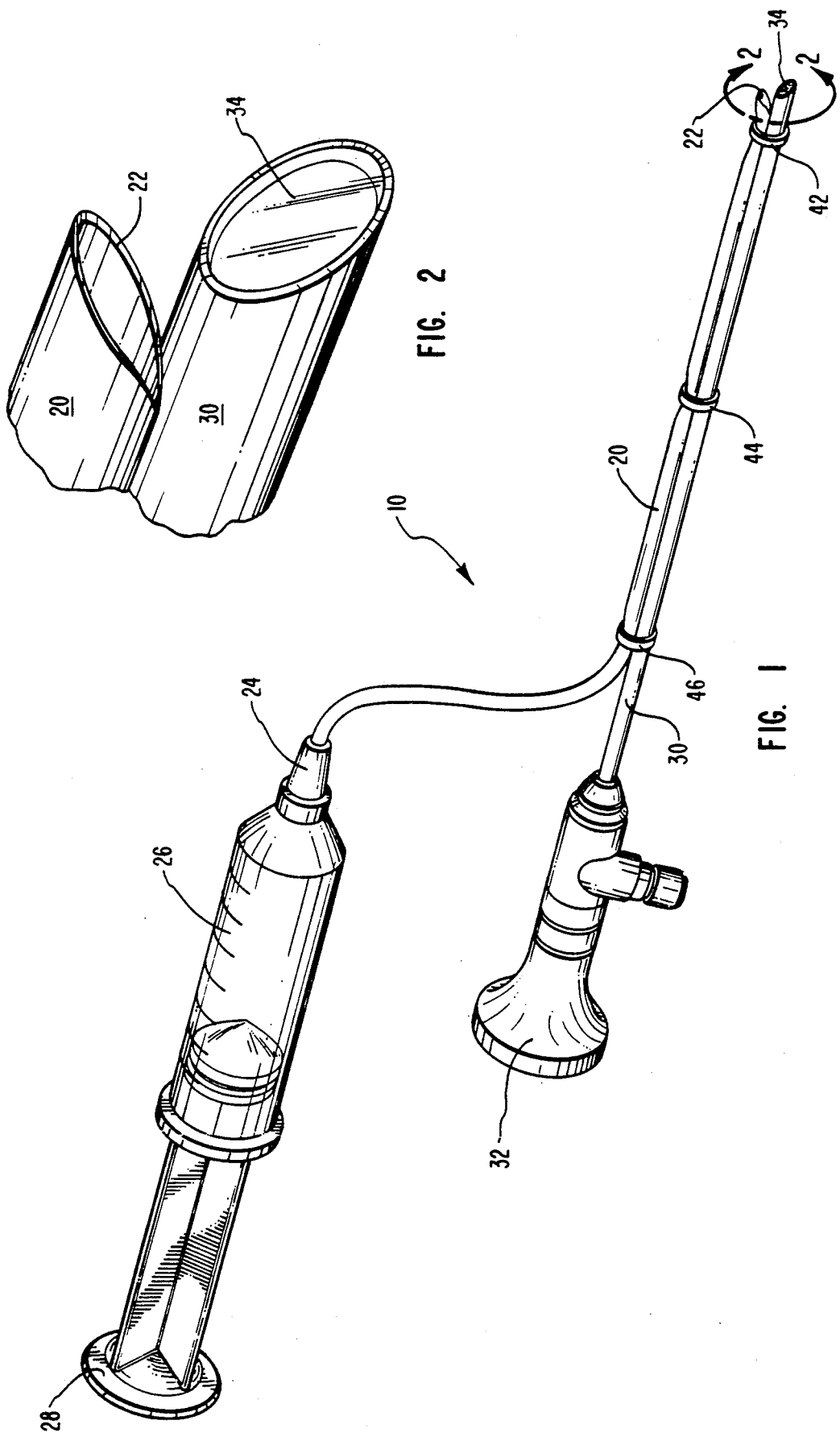
FIG. 1 is a perspective view illustrating a system for use in maintaining a clear visual field during endoscopic procedures in accordance with one presently preferred embodiment of the present invention.
FIG. 2 is an enlarged perspective view of the portion of the embodiment of FIG. 1 designated by line 2—2 in FIG. 1.

It will be readily understood that the components of the present invention, as generally described and illustrated in the Figures herein, could be arranged and designed in a wide variety of different configurations. Thus, the following more detailed description of the embodiment of the system and method of the present invention, as represented in FIGS. 1 and 2, is not intended to limit the scope of the invention, as claimed, but it is merely representative of one presently preferred embodiment of the invention.

The presently preferred embodiment of the invention will be best understood by reference to the drawings, wherein like parts are designated by like numerals throughout.

The system of the present invention, generally designated at 10, is illustrated in its entirety in FIG. 1. As shown, system 10 comprises a tube 20 which is connected to an endoscope 30, the distal end 22 of tube 20 being positioned adjacent lens 34 of endoscope 30. A syringe 26 is connected to tube 20 such that fluid can be injected through tube 20 to clear lens 34.

Endoscope 30 is illustrated herein as a conventional nasal sinus telescope having conventional eyepiece 32 and a forward-oblique (typically 25 degree to 30 degree) angle of view. System 10 of the present invention may, however, be used with telescopes having other angles of view, including, for example, a lateral (typically 70 degree) angle of view and a straight forward (approximately 0 degree) angle of view. Further, system 10 may be useful with other types of surgical telescopes, including telescopes being used for purposes other than nasal sinus surgery.

While tube 20 may be formed of a number of different materials consistent with the general objects and purposes of this invention, tube 20 is preferably resilient so as to minimize interference with the use of endoscope 30. Thus, for example, tube 20 may be formed of a silastic plastic material.

When used in connection with the illustrated form of nasal sinus endoscope, tube 20 may be approximately 3/32 inch (2 mm) in diameter at approximately 15 inches (38 cm) long or longer. For example, tube 20 may be a #5 infant feeding tube such as is currently available from Baxter Healthcare Corporation as catalog No. K32. The specific diameter and length of tube 20 may, however, be varied depending upon the specific needs of the surgeon during a particular surgical procedure.

The distal end 22 of tube 20 is preferably cut at an angle, as shown, so as to form an oblique opening. Importantly, this oblique opening at distal end 22 of tube 20 preferably faces endoscope 30, as shown best in FIG. 2. In this way, the surface tension of fluid leaving tube 20 will assist in conveying the fluid along endoscope 30 to wash lens 34.

Tube 20 is attached to endoscope 30 by means of fasteners 42, 44, and 46. Fasteners 42, 44, and 46 may, for example, comprise suitable elastic bands. When the size of tube 20 is as specified above, small dental elastics having an outside diameter of approximately ¼ inch (6–7 mm) have been found to work acceptably. Alternatively, fasteners 42, 44 and 46 might be resilient loops formed as an integral part of tube 20 itself or might comprise small metal clips.

The proximal end of tube 20 is connected to a syringe 26. Accordingly, tube 20 might be provided with a resilient socket 24, as shown. Syringe 26 may have virtually any suitable size, shape and configuration. As presently preferred, syringe 26 has an internal volume of approximately 20 to 30 cubic centimeters.

In preparing to use the irrigation system 10 of the present invention, a surgical assistant would place tube 20 along endoscope 30 such that the distal end 22 of tube 20 lies adjacent to but does not obstruct lens 34. Advantageously, tube 20 may be positioned along the top, side or bottom of endoscope 30, as determined by the surgeon's specific needs. For most nasal sinus endoscopic procedures, the top position is presently preferred, as illustrated in FIGS. 1 and 2.

Tube 20 is then secured to endoscope 30 by fasteners 42, 44 and 46. Fastener 42 is preferably positioned approximately 5-6 mm from lens 34, with fastener 44 being positioned approximately 3 cm from fastener 42. Fastener 46, and possibly additional fasteners if needed, then secures the remainder of tube 20 along endoscope 30.

Since fasteners 42, 44 and 46 are quite small, an appropriate tool can be used to assist in the placement of the fasteners. When fasteners 42, 44 and 46 comprise dental elastics, for example, the use of a hemostat or other similar instrument may greatly facilitate the placement of the fasteners.

As a final preparation, a syringe 26 is filled with a suitable washing fluid, such as, for example, a sterile saline solution Syringe 26 is then connected to tube 20, and irrigation system 10 is ready for use.

During the surgical procedure, lens 34 of endoscope 30 may periodically become obstructed by fog, blood, tissue fragments or other debris. At such times, piston 28 of syringe 26 may be actuated so as to force fluid through tube 20. Upon leaving the distal end 22 of tube 20, the fluid washes lens 34 and thus maintains a clear visual field.

From the above discussion, it will be appreciated that the present invention provides a system and method for maintaining a clear visual field adjacent the distal viewing window of an endoscope which is simple to assemble and easy to handle and use. Significantly, there are not separate instruments for the surgeon to operate. The surgeon's hands thus remain free to use surgical instruments, suction, and other devices without interruption, and the surgical procedure is thus greatly expedited.

The present invention also provides a system with minimal weight and bulk. The system is thus very easy to control and gives the surgeon better access and a larger viewing area to surgical sites, with only minimal restriction of scope movement. The reduced weight of the system also minimizes surgeon hand fatigue and thus enhances safety during surgery.

The irrigation system of the present invention is also very versatile, since the irrigation tube can be placed along the scope in virtually any manner suited to the surgeons needs. The system is also inexpensive and disposable, thus eliminating the need for time consuming and costly sterilization and maintenance procedures.

The present invention may be embodied in other specific forms without departing from its spirit or essential characteristics. The described embodiment is to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A system for maintaining a clear visual field during endoscopic procedures, the system comprising:
    a substantially rigid endoscope having a distal viewing window;
    a resilient tube having a proximal end and a distal end, the tube being attached to said endoscope such that the distal end of the tube is in proximity to said distal viewing window of the endoscope; and
    means connected to the proximal end of the resilient tube for selectively forcing fluid through the tube and out of the distal end thereof.

2. A system as defined in claim 1 wherein the distal end of the resilient tube forms an oblique angle with respect to a longitudinal axis of the tube.

3. A system as defined in claim 2 wherein the resilient tube is attached to said endoscope such that the oblique opening formed by the distal end of the tube substantially faces the endoscope.

4. A system as defined in claim 1 wherein the resilient tube has an outside diameter of approximately two millimeters.

5. A system as defined in claim 1 wherein the resilient tube is formed of a silastic plastic material.

6. A system as defined in claim 1 wherein the resilient tube is attached to the endoscope by means of elastic bands which encircle both the tube and the endoscope.

7. A system as defined in claim 1 wherein the means for selectively forcing fluid through the tube comprises a syringe.

8. A system as defined in claim 7 wherein the syringe has a fluid capacity within the range of from approximately twenty to approximately thirty cubic centimeters.

9. A system as defined in claim 7 wherein the resilient tube has a resilient socket on the proximal end thereof and wherein the syringe is connected to said resilient socket.

10. A nasal sinus endoscope system, comprising:
    a substantially rigid nasal sinus endoscope having a distal viewing window;
    a resilient tube having a proximal end and a distal end, the tube being attached to the endoscope such that the distal end of the tube is in proximity to the distal viewing window of the endoscope; and
    a syringe connected to the proximal end of the resilient tube for selectively forcing fluid through the tube and out of the distal end thereof.

11. A nasal sinus endoscope system as defined in claim 10 wherein the nasal sinus endoscope is a forward oblique endoscope.

12. A nasal sinus endoscope system as defined in claim 10 wherein the distal end of the resilient tube forms an oblique angle with respect to a longitudinal axis of the tube.

13. A nasal sinus endoscope system as defined in claim 12 wherein the resilient tube is attached to said endoscope such that the oblique opening formed by the distal end of the tube substantially faces the endoscope.

14. A nasal sinus endoscope system as defined in claim 13 wherein the resilient tube is attached to the endoscope by means of elastic bands which encircle both the tube and the endoscope.

15. A nasal sinus endoscope system as defined in claim 14 wherein the resilient tube has an outside diameter of approximately two millimeters.

16. A nasal sinus endoscope system as defined in claim 15 wherein the syringe has a fluid capacity within the range of from approximately twenty to approximately thirty cubic centimeters.

17. A method for maintaining a clear visual field during endoscopic procedures, the method comprising the steps of:
    attaching a resilient tube to a substantially rigid endoscope, the tube having a proximal end and a distal end and the endoscope having a distal viewing window, the tube being attached to the endoscope such that the distal end of the tube is in proximity to the distal viewing window of the endoscope without obstructing said viewing window; and selectively forcing fluid through the tube and out of the distal end thereof so as to clear the distal viewing window of the endoscope.

18. A method as defined in claim 17 wherein the endoscope is a nasal sinus endoscope.

19. A method as defined in claim 17 wherein the distal end of the resilient tube forms an oblique angle with respect to a longitudinal axis of the tube and wherein the step of attaching the tube to the endoscope comprises positioning the tube such that the oblique opening formed by the distal end of the tube substantially faces the endoscope.

20. A method as defined in claim 17 wherein the resilient tube has an outside diameter of approximately two millimeters.

21. A method as defined in claim 17 wherein the step of attaching the resilient tube to the endoscope comprises placing at least one elastic band around both the tube and the endoscope.

22. A method as defined in claim 21 wherein one said elastic band is placed within the range of from approximately five millimeters to approximately six millimeters from the distal viewing window of the endoscope.

23. A method as defined in claim 22 wherein a second said elastic band is placed approximately three and one-half centimeters from the distal viewing window of the endoscope.

24. A method as defined in claim 17 wherein the step of selectively forcing fluid through the tube comprises the steps of:
  connecting a syringe to the proximal end of the tube;
  filling the syringe with fluid; and
  selectively actuating the syringe so as force fluid from the syringe and through the tube.

25. A system for maintaining a clear visual field adjacent a distal viewing window of an endoscope, the system comprising:
  a resilient tube having a proximal end and a distal end, the tube being attached to said endoscope such that the distal end of the tube is in proximity to said distal viewing window of ht endoscope, and the tube being attached to the endoscope by means of fasteners which at least partially encircle the endoscope; and
  means connected to the proximal end of the resilient tube for selectively forcing fluid through the tube and out of the distal end thereof.

26. A nasal sinus endoscope system, comprising:
  a nasal sinus endoscope having a distal viewing window;
  a resilient tube having a proximal end and a distal end, the tube being attached to the endoscope such that the distal end of the tube is in proximity tot he distal viewing window of the endoscope, the distal end of the tube forming an oblique angle with respect to a longitudinal axis of the tube, the tube being attached to said endoscope such that the oblique opening formed by the distal end of the tube substantially faces the endoscope, and the tube being attached to the endoscope by means of fasteners which at least partially encircle the endoscope; and
  a syringe connected to the proximal end of the resilient tube for selectively forcing fluid through the tube and out of the distal end thereof.

27. A nasal sinus endoscope system as defined in claim 26 wherein the resilient tube has an outside diameter of approximately two millimeters.

28. A nasal sinus endoscope system as defined in claim 27 wherein the syringe has a fluid capacity within the range of from approximately twenty to approximately thirty cubic centimeters.

29. A method for maintaining a clear visual field during endoscopic procedures, the method comprising the steps of:
  attaching a resilient tube to an endoscope, said attaching step comprising placing at least one fastener around both the tube and the endoscope, the tube having a proximal end and a distal end and the endoscope, the tube having a proximal end and a distal end and the endoscope having a distal viewing window, the tube being attached to the endoscope such that the distal end of the tube is in proximity to the distal viewing window of the endoscope without obstructing said viewing window; and
  selectively forming fluid through the tube and out of the distal end thereof so as to clear the distal viewing window of the endoscope.

30. A method as defined in claim 29 wherein one said fastener is placed within the range of from approximately five millimeters to approximately six millimeters from the distal viewing window of the endoscope.

31. A method as defined in claim 30 wherein a second said fastener is placed approximately three and one-half centimeters form the distal viewing window of the endoscope.

32. A system for maintaining a clear visual field adjacent a distal viewing window of an endoscope, the system comprising:
  a resilient tube having a proximal end and a distal end, the tube being attached to said endoscope such that the distal end of the tube is in proximity to said distal viewing window of the endoscope, and the tube being attached to the endoscope by means of elastic bands which encircle both the tube and the endoscope; and
  means connected to the proximal end of the resilient tube for selectively forcing fluid through the tube and out of the distal end thereof.

33. A nasal sinus endoscope system, comprising:
  a nasal sinus endoscope having a distal viewing window;
  a resilient tube having a proximal end and a distal end, the tube being attached to the endoscope such that the distal end of the tube is in proximity to the distal viewing window of the endoscope, the distal end of the tube forming an oblique angle with respect to a longitudinal axis of the tube, the tube being attached to said endoscope such that the oblique opening formed by the distal end of the tube substantially faces the endoscope, and the tube being attached to the endoscope by means of elastic bands which encircle both the tube and the endoscope; and
  a syringe connected to the proximal end of the resilient tube for selectively forcing fluid through the tube and out of the distal end thereof.

34. A nasal sinus endoscope system as defined in claim 33 wherein the resilient tube has an outside diameter of approximately two millimeters.

35. A nasal sinus endoscope system as defined in claim 34 wherein the syringe has a fluid capacity within the range of from approximately twenty to approximately thirty cubic centimeters.

36. A method for maintaining a clear visual field during endoscopic procedures, the method comprising the steps of:

attaching a resilient tube to an endoscope, said attaching step comprising placing at least one elastic band around both the tube and the endoscope, the tube having a proximal end and a distal end and the endoscope having a distal viewing window, the tube being attached to the endoscope such that the distal end of the tube is in proximity to the distal viewing window of the endoscope without obstructing said viewing window; and selectively forcing fluid through the tube and out of the distal end thereof so as to clear the distal viewing window of the endoscope.

37. A method as defined in claim 36 wherein one said elastic band is placed within the range of from approximately five millimeters to approximately six millimeters from the distal viewing window of the endoscope.

38. A method as defined in claim 37 wherein a second said elastic band is placed approximately three and one-half centimeters from the distal viewing window of the endoscope.

* * * * *

UNITED STATES PATENT AND TRADEMARK OFFICE
CERTIFICATE OF CORRECTION

PATENT NO. : 5,167,220

DATED : December 1, 1992

INVENTOR(S) : Cathy K. Brown

It is certified that error appears in the above-identified patent and that said Letters Patent is hereby corrected as shown below:

```
In column 1, line 51, after "continue" please insert --.--.
In column 3, line 35, after "endoscope" please insert --.--.
In column 3, line 41, after "drawings" please insert --.--.
In column 5, line 16, after "solution" please insert --.--.
In column 6, line 38, please delete ".is" and insert therefor --is--.
In column 7, line 41, please delete "ht" and insert therefor --the--.
In column 7, line 53, please delete "tot he" and insert therefor --to the--.
In column 8, lines 10-12, please delete "the tube having a proximal end and a distal end and the endoscope"
In column 8, line 19, please delete "forming" and insert therefor --forcing--.
```

Signed and Sealed this

Tenth Day of May, 1994

Attest:

BRUCE LEHMAN

*Attesting Officer*  *Commissioner of Patents and Trademarks*